United States Patent
Schaeffer et al.

(10) Patent No.: US 7,418,399 B2
(45) Date of Patent: Aug. 26, 2008

(54) METHODS AND KITS FOR MANAGING DIAGNOSIS AND THERAPEUTICS OF BACTERIAL INFECTIONS

(75) Inventors: Anthony J. Schaeffer, Hinsdale, IL (US); Ophir Frieder, Chicago, IL (US)

(73) Assignees: Illinois Institute of Technology, Chicago, IL (US); Northwestern University, Evanston, IL (US)

( * ) Notice: Subject to any disclaimer, the term of this patent is extended or adjusted under 35 U.S.C. 154(b) by 986 days.

(21) Appl. No.: 09/972,762

(22) Filed: Oct. 5, 2001

(65) Prior Publication Data

US 2002/0107641 A1 Aug. 8, 2002

Related U.S. Application Data

(63) Continuation-in-part of application No. 09/266,131, filed on Mar. 10, 1999, now abandoned.

(51) Int. Cl.
*G06Q 10/00* (2006.01)
(52) U.S. Cl. .................... 705/2; 705/3; 600/300
(58) Field of Classification Search ............ 705/2, 705/3; 600/300
See application file for complete search history.

(56) References Cited

U.S. PATENT DOCUMENTS

| | | | | | |
|---|---|---|---|---|---|
| 4,024,256 | A | * | 5/1977 | Griffith et al. | 514/244 |
| 4,766,542 | A | | 8/1988 | Pilarczyk | 705/3 |
| 5,508,912 | A | | 4/1996 | Schneiderman | 705/3 |
| 5,542,420 | A | | 8/1996 | Goldman et al. | 600/301 |
| 5,642,936 | A | * | 7/1997 | Evans | 600/300 |
| 5,784,635 | A | * | 7/1998 | McCallum | 712/32 |
| 5,860,917 | A | * | 1/1999 | Comanor et al. | 600/300 |
| 5,911,132 | A | * | 6/1999 | Sloane | 705/3 |
| 5,940,802 | A | * | 8/1999 | Hildebrand et al. | 705/3 |
| 6,000,828 | A | * | 12/1999 | Leet | 705/2 |
| 6,032,146 | A | * | 2/2000 | Chadha et al. | 707/6 |
| 6,242,463 | B1 | * | 6/2001 | Reitberg | 514/317 |
| 6,283,923 | B1 | * | 9/2001 | Finkelstein et al. | 600/532 |
| 6,487,520 | B1 | * | 11/2002 | Kurtzberg et al. | 702/183 |
| 6,537,772 | B1 | * | 3/2003 | Alarcon et al. | 435/34 |
| 7,058,616 | B1 | * | 6/2006 | Larder et al. | 706/15 |

(Continued)

OTHER PUBLICATIONS

Grau, S. et al., "Monitoring of Antimicrobial therapy by an integrated computer program," Aug. 1999, Pharmacy World & Science, vol. 21, p. 152-157.*

(Continued)

*Primary Examiner*—C Luke Gilligan
*Assistant Examiner*—Lena Najarian
(74) *Attorney, Agent, or Firm*—Pauley Petersen & Erickson

(57) ABSTRACT

A method for the construction and utilization of a medical records system capable of providing a continuous data stream of epidemiological data to the records system via kits provided to the symptomatic population to obtain and record an epidemiological profile in a searchable database by applying data mining or automated intelligence techniques whereby, when a valid epidemiological profile is established in the database, automated diagnosis and prescription of treatment may be had for patients presenting similar symptoms. Knowledge discovery techniques may further operate on the database to provide suggested courses of treatment for a virtual class of patients, epidemic threat awareness, and knowledge of drug resistance mutations by a pathogen without direct query of the database.

31 Claims, 2 Drawing Sheets

U.S. PATENT DOCUMENTS

| | | | |
|---|---|---|---|
| 2002/0062315 A1* | 5/2002 | Weiss et al. | 707/100 |
| 2002/0081606 A1* | 6/2002 | Trieu-Cuot et al. | 435/6 |
| 2002/0128860 A1* | 9/2002 | Leveque et al. | 705/2 |

OTHER PUBLICATIONS

Engel et al., 1980, J. Urol. 123:190-191.
Fihn et al., 1988, Ann. Int. Med. 108:350-357.
Fowler and Pulaski 1981, New Engl. J. Med. 304:462-465.
Harding et al., 1979, J.A.M.A. 242:1975-1977.
Hardling et al., 1982, Rev. Infect. Dis. 4:438-443.
Hooton et al., 1991, Antimicrob. Agents Chemother. 35:1479-1483.
Inter-Nordic Urinary Tract Infection Study Group, 1988, Scand. J. Infect. Dis. 20:619-624.
Johnson and Stamm, 1989, Ann. Intern. Med., 111:906-917.
Klotman, 1985, Kidney 18:1-4.
Komaroff, 1984, New Engl. J. Med., 310:368-375.
Kraft and Stamey, 1977, Medicine 56:55-60.
Nicolle et al., 1989, Antimicrob. Agents Chemother. 33:1032-1035.
Nicolle and Ronald, 1987, Infect. Dis. Clin. N. Amer. 1:793-805.
Norrby, 1990, Rev. Infect. Dis. 12:458-467.
Pels et al., 1989, J.A.M.A. 262:1221-1224.
Pfau et al., 1983, J. Urol. 129:11531157.
Ronald et al., 1992, Infection 20:S276-279.
Stamm et al., 1980, Ann. Intern. Med. 92:770-775.
Stamm et al., 1982, New Engl. J. Med. 307:463-468.
Stamm et al., 1982, Rev. Infect. Dis. 4:484-490.
Stamm and Hooton, 1993, New Engl. J. Med. 329:1328-1334.
Vosti 1979, J.A.M.A. 231:934-940.
Wong et al., 1985, Ann. Int. Med. 102:302-307.
Woolfson and Hooper 1989, Antimicrob. Agents Chemother. 33:1655-1661.

* cited by examiner

| NAME | GENDER | AGE | NUMBER of OCCURRENCE | TYPE of UTI |
|---|---|---|---|---|
| Sara Klein | F | 33 | 1 | not complicated |
| Tom Gross | M | 35 | 1 | complicated |
| Sally Weiss | F | 23 | 4 | complicated |
| Fred Schwartz | M | 29 | 1 | complicated |
| Susan Brown | F | 11 | 1 | complicated |
| Jody Stark | F | 30 | 1 | not complicated |
| Mary Smith | F | 46 | 1 | not complicated |
| Kelly Jones | F | 43 | 1 | not complicated |
| Tammy Green | F | 39 | 1 | not complicated |
| David Gold | M | 62 | 2 | complicated |

METHODS AND KITS FOR MANAGING DIAGNOSIS AND THERAPEUTICS OF BACTERIAL INFECTIONS

The present invention is a Continuation In Part of U.S. patent application Ser. No. 09/266,131, filed Mar. 10, 1999, now abandoned entitled, "Methods and Kits for Managing Diagnosis and Therapeutics of Bacterial Infections".

BACKGROUND OF THE INVENTION

The present invention relates to the management of diagnosis and treatment of infections prior to or in the absence of culturing the pathogen prior to commencing treatment.

Epidemiology is the branch of medicine that deals with the study of the causes, incidence, distribution, and control of disease in populations or the sum of factors controlling the presence or absence of a disease or pathogen. "Epidemiology" and forms thereof will be used herein in the broadest sense of all pathogenic, personal, and demographic factors that may be tracked according to the dictates of the present invention.

Symptomatic urinary tract infections (UTIs) are among the most common bacterial infections accounting for more than 7 million outpatient visits to physicians' offices and well over one million hospital admissions in the United States annually. In ambulatory patients alone, the national health care cost of uncomplicated lower UTIs is estimated to approach $1 billion. At a time when controlling spiraling health care costs is a national priority, improvements in the management of UTI is imperative.

Currently, when a patient pays an office visit to the doctor complaining of the symptoms of UTI, a presumptive diagnosis is made by examining the urine microscopically for microorganisms or by performing an indirect dipstick test that measures a microbial metabolite. Although these tests may reveal the presence of a microbial infection, they do not identify the type of bacterium present or indicate the drug sensitivity of the bacterium. Moreover, a urine culture is not typically performed if the patient appears to have an uncomplicated UTI; rather, a short course of empirical antimicrobial therapy is given. No follow-up visit or bacterial culture after therapy is necessary unless symptoms persist or recur. If any clinical features or other factors suggest a complicated infection, a bacterial culture is indicated and should be performed before therapy is started. Mitigating factors that would necessitate a culture include diabetes, symptoms for greater than seven days, recent UTI or antimicrobial use, use of a diaphragm, age less than thirteen or greater than sixty-five, and pregnancy.

In principle, the most appropriate antimicrobial to treat an infection could be determined by a clinical microbiology laboratory. That is, the infectious microorganism may be cultured, identified, and tested for drug sensitivity. In practice, this is rarely done because of the expense and because the demand for relief from the symptoms of UTI is too urgent to wait for results of such prolonged testing. As a result of the urgency for prompt treatment, antibiotics are generally prescribed empirically and with variable success.

This empirical method of treating patients without cultures or documentation has significant potential for complications and needless treatment of patients who do not have infections. Approximately ninety-five percent of patients with UTI have no serious risk of complications and empirical treatment is sufficient; however, about five percent have significant risk for complications which can be costly to treat and which can even be life threatening. For instance, if a patient is treated with empirically prescribed antimicrobials for a presumptive infection when in fact she has another more serious condition such as bladder cancer (which often has the same symptoms as UTI), obvious adverse results can ensue from a delay in diagnosis. However, the alternative of requiring repeated physician visits and cultures of all women who present with the symptoms of UTI is clearly inconvenient to the patient and physician and is unnecessarily expensive in the majority of cases. Therefore, there is an acute need for a method of treating routine UTI in an appropriate patient population that conserves health care resources while providing proper treatment to patients with more complicated conditions.

The diagnosis of UTI is complicated by the fact that there is a 48 to 72 hour lead time to obtain information from a urine culture on the type of pathogen and its antimicrobial susceptibility profile. The uncertainty about the proper course of treatment during this period can be reduced if comprehensive up-to-date data are available for the type of patient, regional location of the patient, and the timing of the infection.

Another aspect of increasing concern in UTI management is the growing microbial resistance to existing antibiotics. While there are other infectious diseases such as tuberculosis for which resistance is a serious problem, UTI is unique because of the large number of individuals affected and the difficulty of tracking resistance since cultures are generally not performed under the current treatment scheme. Since patients are generally treated on an outpatient basis, non-responsiveness to drug therapy could be due to drug resistance or to other factors such as non-compliance or misdiagnosis. Furthermore, drug resistant microbial strains can arise and spread very rapidly, but they are often localized within narrow geographical areas of socio-economic groups. Thus, even if there were more historical information available it may have little relevance to the current context due to rapid changes in drug resistance. Thus, drug resistance in any disease must be taken very seriously, but it cannot be monitored without a mechanism of collecting information, e.g., urine cultures.

UTIs are complicated diseases to diagnose and treat because the pathogens involved in causing similar symptoms may vary widely based on region, type of patient, and time. Put another way, UTIs are a heterogeneous disease. The heterogeneous nature arises from two main characteristics of UTIs: 1) there is an inherently variable nature of the pathogen, and 2) different patients may respond differently to the same pathogen and to the same therapeutic regimen. Resistance of the various UTI pathogens to antimicrobials may change due to any of the above, or other, specific factors. Therefore, there is an often unpredictable response of the pathogen to therapy. This is unlike a disease such as hypertension where cause and treatment are relatively predictable and static over time and geography. In the treatment of UTIs neither the cause nor the treatment is predictable unless a great deal of individual data are gathered and great deal is known about the most current state of UTI epidemiology in a particular locality. Current diagnostic practice, record keeping, and reporting of UTI epidemiology are limited relative to the scope of the changing nature of the disease. Further, only fragmented and dated information is gathered, and these data are not linked to relevant clinical data such as the type of patient, infection, or outcome of therapy. Thus, there is no current, comprehensive database, or records, system that would be considered adequate for providing predictable and efficacious treatment.

Additionally, there are other prevalent infections in humans that consume vast amounts of our health care resources besides UTIs. Similarly to UTI, several of these infections are characterized by multiple causative pathogens that cause the same or similar symptoms and the rapid development of drug resistance, which hamper effective diagnosis and antimicrobial therapy. These infections, which include, for example, throat infections and intestinal tract infections, also afflict large numbers of patients and cause large numbers of outpatient and hospital visits each year thereby taking an enormous toll on health care resources. Thus, cost effective and efficacious treatment of infections, including, but not limited to, urinary tract infections, throat infections, and intestinal tract infections, is of paramount importance in this era of spiraling health care costs.

As presented in the above-identified related application, a doctor-directed and controlled, patient processed, "Self-Start" treatment process utilizes a searchable medical record system that is created according to data entered by the patients or diagnostic laboratories or both. Using this medical record system, a medical practitioner is more accurately able to assess the type of bacterium, or pathogen, causing the infection in a previously undiagnosed, i.e., new, patient based on the collected data of previous patients. The practitioner can then further prescribe an empirically effective course of treatment for the infection in the absence of a diagnostic test performed on the new patient.

Specifically, the related application presented methods consist of: collecting information concerning persons previously presenting symptoms; organizing the collected patient information in an electronic medical record system; analyzing the organized information to identify one or more particular pathogens which caused the infection in one or more of the persons from whom the information was collected; for each pathogen identified, identifying personal and/or demographic information common to the persons who developed an infection from the particular pathogen; and identifying one or more antimicrobials which were effective or ineffective in treating the infections developed from the particular pathogen.

The related application also presented methods of establishing a searchable medical record system for assisting a medical practitioner in more accurately predicting a type of pathogen which has caused an infection in a previously undiagnosed human patient and prescribing an effective course of treatment for the infection prior to or in the absence of performing a diagnostic test on a sample from the human patient.

There is a great need in the treatment of UTIs and similar infections to provide timely information on a broad range of specific patient data and treatment efficacy that is readily available to the health care practitioner. Such information must be current and comprehensive to take into account the changing nature of UTI pathogens. Only an integrated system of information gathering, and knowledge retrieval from this information, on the pathogens and their treatment will yield viable results. This integrated system should be done as economically as possible.

While the previously presented systems of the related application, including the searchable medical record system as defined therein, provide a great help to the health care practitioner and to the public health system, all interaction with the data is either data entry initiated by a patient or a laboratory or a query issuance by the physician. Any self-organization or self-discovery processing of the database on its own is presented only as a passing aside. Rather than obtaining all knowledge by direct inquiries from the medical practitioner, it would further be desirable to apply database and knowledge and information discovery techniques to the collected data in an effort to improve public health.

In sum, there is a need for a medical records, or database, system that accurately collects relevant and current clinical data and analyzes the data to predict the causative pathogens and their rapidly changing drug sensitivity for heterogeneous diseases such as UTIs so as to provide effective therapy for infections while minimizing health care costs and the development of drug resistance.

SUMMARY OF THE INVENTION

Embodiments of the present invention provide medical records systems including methods and apparatus for more accurately predicting the causative pathogens and the antimicrobial sensitivity thereof for diagnosis and management of infections. More particularly, the present invention may provide components of a medical records system including kits for the collection of epidemiological information from the individuals of a population exhibiting symptoms of a particular class of disease. Preferably, the kit will include information gathering means whereby information may be gathered about the individual, the disease and the treatment at each stage of the medical process from before clinical diagnosis, through diagnosis and treatment, to after-treatment follow ups. The kits, besides providing personal and demographic information gathering tools, may also include diagnostic tests for identifying a pathogen, and treatments for the pathogen. Preferably the kits are constructed and arranged to require minimal input from the health care practitioners when used in conjunction with a medical records database suitably arranged to accept and structure the collected data and derive useful knowledge from the collected data, especially after a sufficiently large sample of patient data is acquired to render the database conclusions valid. Interaction of the database with the health care practitioner's input is, of course, provided for.

In one aspect of the present invention, the kit may include one or more diagnostic tests for indirect testing or direct testing of pathogen presence. In another aspect, a self-administered kit is provided to each patient to obtain at least a portion of the patient information. Further, the kit may include a first diagnostic test for the person to obtain the first sample to identify the pathogen, and a second diagnostic test for the person to obtain the second sample to determine the efficacy of treatment. The kit may further include a prescribed dose of an antimicrobial or other medicine used to treat the suspected or confirmed pathogen.

In yet another aspect, the kit may include a means for gathering the personal, demographic and other epidemiological information of the person having the symptoms, e.g., a form of some type. The form may be selected from the group consisting of a form for the person to provide the epidemiological information before commencing a course of treatment, a form for the person to provide the results of the diagnostic test before or after commencing a course of treatment, and a form for the person to provide the results of the completed course of treatment. The information collected may concern the success of, failure of, or any adverse reaction to, treatments used by the person.

In addition, the kit may include a prescription fulfillment report card to be filled out by a pharmacist or physician dispensing said kit to be returned to an entity collecting the information and instructional material for using the kit.

It will be appreciated that the kit may be provided in many alternative forms and further may be provided to, and designed for, any link in the health care chain from patient to trained health care practitioner to the medical records management entity, in any combination.

Ultimately as the database becomes valid, the invention can provide means of diagnosing and treating an infection in a previously undiagnosed patient without first performing a diagnostic test on a sample from the patient. An exemplary embodiment of the medical records system may comprise:

a) providing a kit to each of a plurality of members of a population presenting symptoms associated with a particular disease, the kit having means for collecting prior epidemiological information of members of the population previously having symptoms similar to those of the patient;

b) entering and storing the collected epidemiological information in an electronic database;

c) creating an automated knowledge discovery system including organizing the prior epidemiological information in the electronic database to make the epidemiological information amenable to data mining;

d) providing a similar kit to the patient for collecting epidemiological information of the patient;

e) entering at least some of the patient information into a query function of said database;

f) data mining the organized epidemiological information to predict a pathogen infecting the patient based on similarities of the patient information with the organized epidemiological information; and g) prescribing a course of treatment to the patient based on the prediction of the data mining;

h) whereby the patient with symptoms of an infection may be diagnosed or treated or both before testing for the presence of specific pathogens which may be infecting the patient.

Thus, the present invention includes means for establishing a searchable medical record system for assisting a medical practitioner in more accurately predicting the type of pathogen, which has caused an infection in a previously undiagnosed human patient, and in more accurately prescribing an effective course of treatment prior to performing a diagnostic test on a sample from the patient.

The present invention further includes various techniques for constructing and utilizing a database for the searchable medical record system. Once the collected data are stored in a searchable medical record system, the present invention provides for knowledge discovery operations to continuously execute on those data. These knowledge discovery operations derive suggestions, e.g., treatment patterns or guidance procedures, that can be presented to the physician. These suggestions are self generated within the database operations and provide knowledge to the physician through learning based on the data stored and past decisions made. Eventually, the doctor may examine the knowledge provided by the systems of the present invention and will then be able to comment on the degree of validity or value of the given suggestions, and then further return doctor comments back to the knowledge discovery system.

The knowledge discovery system, may, in turn process the newly obtained guidance, e.g., doctor comments, and store this information in the database. Based on this information, various manipulation routines can execute and potentially new therapeutic guidelines can be derived. Whenever new suggestions are derived by the knowledge discovery system, the suggestions are either saved for later processing or are directly forwarded to the physician. The present invention enhances the functionality of the originally described diagnostic system by providing additional functionality that derives timely, up-to-date, treatment guidance for the physician in addition to the previously disclosed query processing capability.

The knowledge discovery system of the present invention can utilize various data mining techniques to further enhance the efficacy of the previously disclosed diagnostic system. There are many data mining approaches, and new approaches are being continually developed, which may be known to the person having ordinary skill in the art of information technologies. Thus, the systems and methods described herein are intended simply to serve as representative algorithms and the present invention is not intended to be limited to the examples set forth herein. The present invention teaches the use of data mining approaches to better predict the pathogen encountered and to provide better medical practitioner guidance with respect to the undiagnosed patient. This is particularly crucial within this application since susceptibilities and tolerance to pathogen mutations and their treatment rapidly change.

The discovery of knowledge from the data can follow a process comprising iterative refinement of the following steps: data cleaning with the potential integration of data from several sources, data transformation to a common format, data mining, and pattern evaluation and knowledge representation.

Generally, "data cleaning" involves the review of the data set, potentially removing or correcting erroneous data; "data transformation" involves the transformation of the data to a common format that supports data mining; and "data mining" detects patterns found in the data, derives knowledge from the patterns, and represents the knowledge to the appropriate persons. Validation and evaluation of the detected patterns and the representation of knowledge are the last of the iterative steps in the knowledge discovery process.

By practice of the techniques according to the present invention, data may be made available to the health practitioners in preanalyzed formats and suggested courses of practice without, or in addition to, the previously taught system of data extraction by direct query from the health practitioner. Knowledge discovery processing, including the above data mining techniques, as set forth herein can be applied to continuously changing data. Data changes may arise from such causes as additional patient data entered in to the system or the discovery of new bacterial resistance. Best practice guidelines for the physician can be derived according to the techniques herein. Potential epidemic threat detection and warning can be accomplished by the present invention through data related to group diagnostic patterns and derived information potentially based on geographic regions, age, weight, profession, etc. Predictive treatment outcome generation via a "virtual patient" can be supported to develop answers to hypothetical scenarios by automatically mining the data to derive potential treatment patterns. Experimentation on a virtual patient or class of groups of patients is supported. Further, given the cleansing process involved in knowledge discovery, error detection, with potential for suggestive correction, is supported.

BRIEF DESCRIPTION OF THE DRAWING

For the purpose of illustrating the invention, there are shown in the drawings embodiment(s) that are presently preferred. It should be understood, however, that the invention is not limited to the precise arrangements and instrumentalities shown. In the drawings.

DETAILED DESCRIPTION OF THE INVENTION

Figure 1:
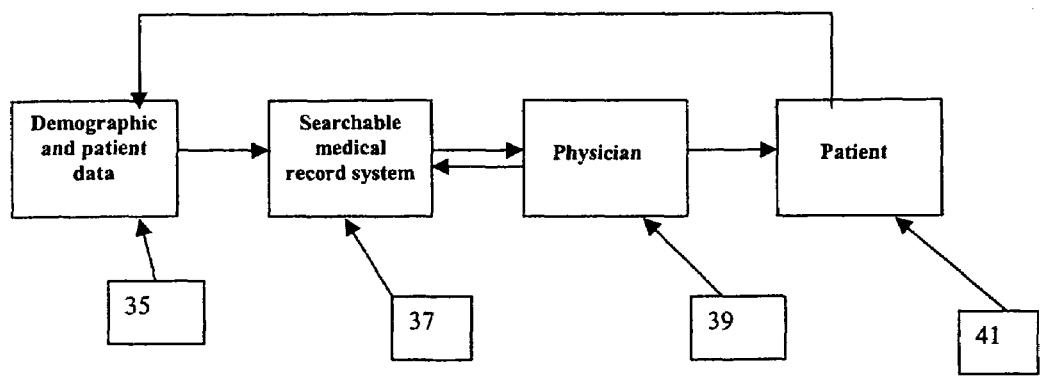
FIG. 1 is a block diagram of the medical records system according to the parent application.

The present invention provides medical records systems including means and methods for obtaining and comparing epidemiological, e.g., demographic, personal, and medical data concerning persons previously diagnosed and treated for infections with the same or similar data from a particular, previously undiagnosed, patient presenting with, i.e., having, the same or similar symptoms of infection. The present invention thus allows prediction, or diagnosis, for the particular patient, of the most likely pathogen to the causative agent of the infection and prediction, or prescribing, of an effective treatment for the infection. The diagnosis and prescription may preferably be done for the patient prior to, or in the absence of, obtaining a sample, and analyzing the sample, from the particular patient. For simplicity, the phrase "prior to" will be understood to include "in the absence of" hereinafter unless otherwise indicated.

An exemplary embodiment of the present invention comprises an integrated, multi-component method and system designed to lower the cost of treatment, for example, of bacterial urinary tract infections (UTIs) while simultaneously improving the quality of patient care. It also provides a systematic method for the collection of data that will enable vigilant monitoring of the host and bacterial factors associated with bacterial infections. The components of the medical records system may include (1) a "self-start" kit for home diagnosis, sample gathering mechanisms, and data collection, and (2) a database for storing the collected data and applying data mining tools to the data for automated knowledge discovery.

Although a detailed illustrative embodiment of the present invention is disclosed herein, specific communications systems, information storage formats, health data processing structures, and so on, may be embodied in a wide variety of alternatives, some of which may be quite different from those of the disclosed embodiment. Consequently, the specific structural and functional details disclosed herein are merely representative; yet in that regard, they are deemed to afford the best embodiment for purposes of disclosure and to provide a basis for the claims herein, which define the scope of the present invention.

The exemplary embodiment includes a method of establishing a medical record system providing automated knowledge discovery in predicting a type of bacterium which has caused a bacterial infection in a previously undiagnosed human patient and predicting an effective course of treatment for the bacterial infection prior to performing a diagnostic test on a sample from the human patient.

The Information

The method comprises (1) initially collecting epidemiological information concerning persons presenting with symptoms typical of bacterial infections from a variety of sources. The information concerning such persons may include, but is not limited to: sex, age, race, ethnic background, address, weight, height, place of employment, type of work performed, income, median annual family income, social history, along with a multitude of additional information including such parameters as habits, health and conditions of the individuals including medical history and such parameters as blood pressure, urine culture, stool culture, throat culture, history of antimicrobial use, history of any known drug allergies, and a history of past and present infections (i.e., persistent, chronic, recurrent, date of last infection, and the like). For each such past infection, information may be gathered on: the effectiveness of antimicrobials in treating past infections, the type of bacterium causing it, the type, dose and duration of antimicrobial treatment, the outcomes of such antimicrobial treatment, and whether there were any adverse effects to the antimicrobial treatment. The information may also include any known risk factors for various types of bacterial infections such as, for example, whether the person is a diabetic, pregnant, immunosuppressed, catheterized, and the like.

The subject information for such persons may be obtained from several sources, e.g., medical providers' offices, laboratories, hospitals, wellness centers, and the individual patients themselves, via forms filled out and collected in any of a variety of ways or means of communication.

Ultimately the epidemiological information is received by an information collecting, or database, entity where the information may be categorized, stored, processed and conveniently retrieved. However, data storage and processing do not necessarily have to be performed by the same entity but may be accomplished by one or more persons or entities. Further, if there is more than one information storage center, the information center need not be physically located in any one particular geographic location; instead, various information storage centers may be connected to one another such that data may be shared or exchanged by one or more centers such that all or some portion of the information may be accessible for data analysis by one or more centers. However, each information center may also stand alone and may function individually in collecting, organizing, searching and analyzing information.

In addition to collecting the above-stated information, the invention may encompass obtaining a first sample from each person prior to the initiation of treatment for the bacterial infection. "Sample", as used herein, means any fluid or tissue from a patient.

Upon obtaining a sample from each person, a diagnostic test can be performed. "Diagnostic test", as used herein, means any method by which the presence and/or identity of a bacterium is determined in a sample or by which the susceptibility of a bacterium to an antimicrobial is determined. In one embodiment, the diagnostic test is a direct diagnostic test. "Direct diagnostic test", as used herein, means a test performed to directly detect the bacterium in the sample. Alternatively, an indirect diagnostic test may be used to identify the bacterium that caused the bacterial infection. "Indirect diagnostic test," as used herein, means any test that detects the absence or presence of bacterial metabolites or some other substance that provides immediate evidence, without directly detecting the bacterium, that the bacterium may be present in the sample.

However, the invention is not limited to requiring that the sample be obtained prior to initiation of treatment. Instead, the invention should also be construed to encompass situations where the sample is obtained at any time before the symptoms of the bacterial infection are resolved or at any time wherein detectable amounts of bacteria would be present in the sample. Further, the persons may obtain the sample or a medical practitioner or some other person or entity may obtain it.

In one embodiment, the information provided by the individual or by another source such as a pharmacy or the prescribing entity, includes the identity of an antimicrobial taken by the person. The information provided might include the type of antimicrobial taken for a urinary tract infection, and the name of the pharmacy that filled the prescription, the name and address of the prescribing entity, and the amount, dosage, and duration of the antimicrobial treatment.

Further, in another aspect of the present invention, a second sample can be obtained after the course of treatment is completed to determine the effectiveness of the prescribed antimicrobial in treating the bacterial infection. That is, the sample is tested to determine whether any detectable evidence of bacteria that caused the infection is present in the sample. The presence or absence of the bacterium and/or bacterial products following the course of treatment is an indicator that the antimicrobial is or is not effective in treating the bacterial infection. This information is also collected and input into the medical record system of the invention.

If the identity of the antimicrobial is provided, then the person's outcome at the completion of the course of treatment also identifies whether the antimicrobial is effective for treating the identified bacterium. That is, whether the symptoms are resolved by completion of the course of antimicrobial treatment is an indicator as to whether the antimicrobial taken is effective in treating the bacterial infection.

All epidemiological information collected is then organized in a searchable medical record system. The term "searchable medical record system", as used herein, means any data storage system wherein the information concerning individuals previously treated or currently being treated for bacterial infection may be stored; and from which the information may be accessed, processed, analyzed, compared across several parameters, or retrieved so as to allow the information concerning a particular patient to be compared to similar information from other persons; and to identify other persons besides the particular patient having presented with similar symptoms and having demographic and/or other medical and personal data similar to the particular patient. Such systems may be as described in, for example, Goldman and Greenberg (U.S. Pat. No. 5,542,420). In this way, as more fully discussed elsewhere herein, the information stored in the system may be compared so as to produce a profile of the particular patient which may be compared to the profiles of the other persons whose information is stored in the record system to determine those previously diagnosed and treated individuals which are most similar to the particular patient. Such data comparison may be performed as described by Schneiderman (U.S. Pat. No. 5,508,912). The data can be analyzed and reprioritized based on current outcomes to determine which data are more predictive of the causative pathogen and/or effective antimicrobial.

In addition, the information concerning each particular patient is input into the system so as to continually add to the information concerning bacterial infections and the susceptibility of bacteria to antimicrobials; thereby providing an ongoing system for predicting causative bacteria and effective antimicrobials in a patient population. One skilled in the art will appreciate that such a database should be self-perpetuating and should take into account any change in the prevalence of a particular bacterium at a particular time, in a particular geographic area, or the like, and would also account for any development of resistance to antimicrobials for each such bacterium as may be seen over time.

"Organizing", as used herein, means that the information in the searchable medical record system is input and processed such that virtually any set, subset, or type of individual patient information may be compared with information from other patients to identify common information amongst the patients and be analyzed to identify one or more individuals who have certain information in common.

The organized information is then analyzed to identify one or more particular bacterium that caused the bacterial infection in one or more persons from whom the information was collected. Thus, the information is analyzed to identify each bacterium that caused an infection in one or more persons previously presenting with symptoms of bacterial infections thereby linking each bacterium with the symptoms and demographic and other information for each person whose information is stored in the record system.

For each bacterium which caused an infection, the information is also analyzed to identify one or more antimicrobials which were effective and/or ineffective in treating the bacterial infection in each person whose infection was caused by the bacterium as identified in the record system. That is, the information is analyzed such that each bacterium is cross-matched with the antimicrobial used to treat it and the information is further analyzed to identify which antimicrobials were effective or ineffective for each bacterium identified in the record system.

It will be appreciated that the accuracy of the prediction will depend on various factors including the number of matching characteristics between the undiagnosed patient and the previous persons, the number of patients whose information is present in the record system, the number of persons in the record system which were afflicted with symptoms similar to those of the undiagnosed patient, the number of persons in the record system whose personal and demographic information match that of the undiagnosed patient, and, of those persons, the number which were infected with any particular bacterium, and the number treated with any particular antimicrobial having a successful or unsuccessful treatment outcome.

The Kit

The present invention may also include a self-administered kit to be provided to each person whose information is to be input into the medical record system. It is noted, however, that pertinent data might be acquired by means other than the use of the self-administered kit. The kit can be provided to, at least in part, obtain the personal and demographic information for the person. The kit is valuable in efficiently and economically obtaining the patient information needed to establish and maintain the medical records system.

The kit may further include a first diagnostic test for the person to obtain a first sample to identify pathogens, and a second diagnostic test for the person to obtain a second sample to determine the efficacy of a prescribed antimicrobial. The first sample is preferably obtained prior to the commencement of treatment while the second diagnostic test to obtain the second sample is to be performed after completion of the antimicrobial course of treatment. Further, the patient may perform the first diagnostic test or it may be sent to a medical practitioner or other entity for evaluation. The first diagnostic test, which is used to obtain a sample prior to initiating antimicrobial treatment, may be used to identify the bacterium present in the sample. The sample may also be used to perform in vitro testing of the effectiveness of various antimicrobials in treating the bacterial infection to identify one or more antimicrobials likely to be effective in treating the bacterial infection caused by the identified bacterium.

Therefore, a person of ordinary skill in the art would appreciate, based on the disclosure provided herein, that the identity of the bacterium and the identity of an antimicrobial likely to be effective in treating an infection caused thereby may be ascertained by obtaining a single sample from a patient without need of further sampling. As stated previously, the effectiveness of the antimicrobial may be further confirmed based on the patient outcome at the end of the course of treatment.

All of this information may be collected and organized into the medical record system to maintain the currency of the information as new antimicrobials are developed and as bacterial resistance to antimicrobials develops over time. In this way, the record system is updated regularly to aid in the diagnosis and treatment for an undiagnosed patient without first obtaining a sample from the undiagnosed patient and avoiding the costs and inconvenience of an office visit for the patient while providing effective patient care.

In one embodiment, the self-administered kit includes a prescribed dose of an antimicrobial predicted by the database applications to be effective in treating the infection in a previously undiagnosed patient based on the fact that the antimicrobial successfully treated previous persons having similar symptoms and similar personal and demographic information to the undiagnosed patient. However, the present invention should not be construed to require that the antimicrobial be included with the self-administered kit. Rather, the antimicrobial may be prescribed any time before or after the self-administered kit is provided to the previously undiagnosed patient, and may be provided separately from the kit.

The kit may also comprise a form provided to the person for the purpose of documenting his or her personal and demographic information. The information may be provided to the medical practitioner providing the kit. The information may be submitted to an entity collecting information for creating and maintaining a medical record system or an entity associated therewith. The information may be provided either in person or by other means of communication. Alternatively, the information may be provided directly by the patient to the medical record system such as, for example, by direct connection to the database such as through the Internet, facsimile device, telephone, or other device for transmitting data.

The invention may include various means or forms for the person to provide a sample or the results of the diagnostic test prior to commencing a course of treatment; and means or forms for submitting a sample or diagnostic test results after completing a course of treatment. The information requested by the form need not be submitted as a form. Rather, the information concerning personal and demographic data may be provided to a medical practitioner or to an entity collecting such information for a medical record system in person, by telephone, or by any other method of communication now known or to be developed. The information requested by the form regarding personal and demographic information should be provided before an antinicrobial is prescribed to the previously undiagnosed patient. This information is the basis to determine the identity of the most likely bacterium and an appropriate antimicrobial via a comparison of the information to the information of other persons in the record system.

The kit may further comprise a prescription fulfillment card to be returned by the pharmacy dispensing the self-administering kit and instructional material for the use of the kit. The prescription fulfillment card can be returned either to the prescribing entity or to an information-collecting center. In this manner, the patients to whom the kit is prescribed are identified and their names and information are entered into the medical record system. Means, either human or electronic, to authenticate the patient's identity and data might likewise be used. This provides a manner of following up with those persons who have symptoms indicative of a bacterial infection so that they may be contacted and their information can be obtained and entered into the record system. The instructional material describes the use of the kit and its various components.

The Database and Its Management

Referencing FIG. 1, there is illustrated a system of the original parent application. Referencing FIG. 2, there is illustrated a system of the additional and overlapping system of the present invention. In the original parent application, demographic and patient specific information, or data, 35 enter the system and are stored in the searchable medical record system, or database 37. The physician, also sometimes referred to herein as the doctor, or the health care practitioner, 39 issues requests (queries) against the database 37 and receives data relevant to the request. From the data received, the physician may formulate an opinion regarding the potential treatment and prescribe this treatment to the patient 41. All interaction with the data is either data entry initiated by a patient or a laboratory or a query issuance by the physician.

Figure 2:
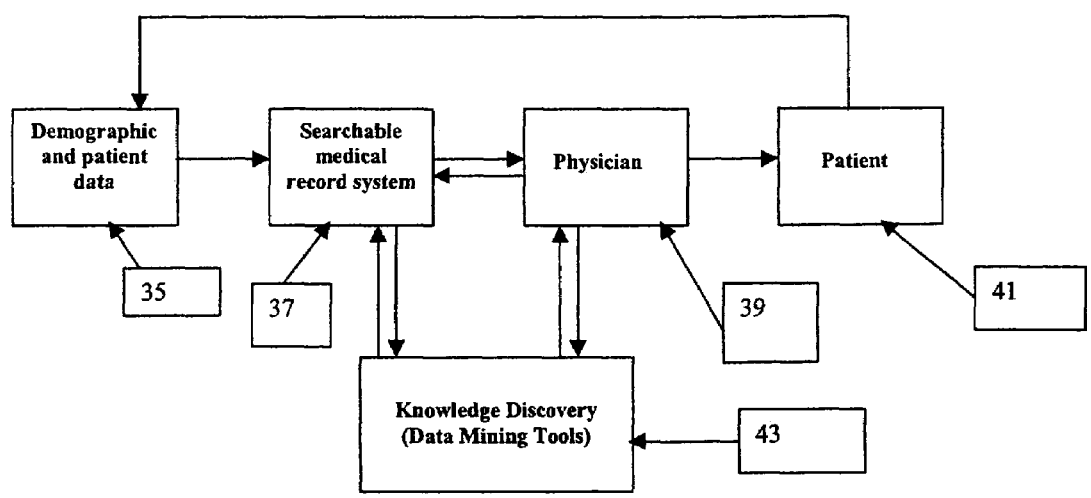
FIG. 2 is a block diagram of the medical records system according to the present application.

Referencing FIG. 2, there is illustrated an embodiment of the present invention wherein knowledge discovery tools 43 operate on the database 37 to provide a more complete information loop consisting of the automated data processing, the database information and the physician to further enhance the information available for the treatment of pathogens and the furtherance of public health.

The automated and enhanced discovery of knowledge for treatment of disease according to the present invention can be accomplished from the gathered data 37 by following a process comprising iterative refinement of one or more of the following steps: data cleaning with the potential integration of data from several sources; data transformation to a common format; data mining; and pattern evaluation and knowledge representation.

"Data cleaning", within the context of the present invention, generally involves the review of the data set, potentially removing or correcting erroneous data. The correction or removal of erroneous data may follow either predefined rules as can be developed for the specific purposes of a particular medical records application, or may follow some heuristic processing pattern such as known in or adapted from the art. This process, or processes, may involve the integration of data that are obtained from multiple sources. The final goal of the data cleaning process is the availability of a single source of correct data.

"Data transformation" involves the transformation of the data to a common format that supports data mining. Such processing can include the conversion of the data to a common measure of units. For example, all temperature readings should be in Celsius as opposed to some in Fahrenheit and others in Celsius. Other data transformation processing can include generalization, namely, all temperatures (in Celsius) in the range of less than 10 degrees, 10 to 25 degrees, and over 25 degrees are grouped as cold, moderate, and hot, respectively. Such generalization is often necessary for some data mining approaches.

"Data mining" approaches, as further described below, have common features in that they detect patterns found in the data from which knowledge is derived and represented. Basically, a working definition of "data mining" is the extraction of knowledge previously unknown. The validation and evaluation of the detected patterns and the representation of knowledge is the last of the iterative steps in the knowledge discovery process.

Data Mining the "Searchable Medical Record System"

Four sample data mining techniques are set forth herein by way of exemplifying means of detecting patterns and deriving knowledge from the stored data. The four techniques are: Discrimination, Association Rules (Analysis), Classification (Decision Trees), and Clustering. The person having ordinary skill in the art will note that there are many other common data mining techniques which are not overviewed herein, but which may be relevant within certain contexts of the present invention, such as those on neural networks and Naïve-Bayesian approaches.

Figures 3, 4:
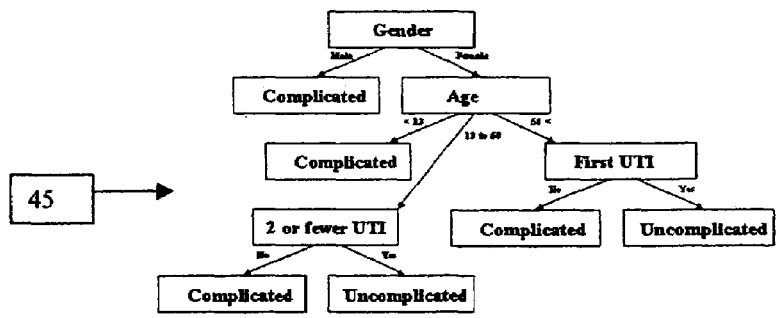
FIG. 3 is a highly simplified hypothetical database of persons presenting symptoms of urinary tract infections for purposes of explaining data mining procedures useful for urinary tract infection diagnosis.
FIG. 4 is a block diagram representing a simplified decision tree for purposes of explaining data mining procedures useful for urinary tract infection diagnosis.

Referencing FIG. 3, there is shown a limited representation of the database that contains hypothetical data entries, as collected according to the above discussion, for people that were previously treated for UTIs. In the first data mining technique, Discrimination based approaches typically partition data into multiple classes. For example, assuming two classes of data, the partition may be those data that support a given situation and those that contradict a given situation. Once properly trained, i.e., a classification scheme is assembled and validated, the system of the present invention can predict potential outcomes for future entries based on the discrimination classes.

For example, one criterion for the determination of the degree of complication of a UTI is gender. As shown, the database consists of ten patient entries with five attributes per entry. Clearly, the patient identification attribute (NAME) does not contribute to the resulting type determination (TYPE of UTI). Thus, the discrimination algorithm sifting through the data recorded in the remaining three attributes (GENDER, AGE, and NUMBER of OCCURRENCE) will determine, for example, that all male patients are diagnosed as having a complicated UTI. Thus, if a new male patient is treated, the system will predict that his diagnosis is a complicated UTI and should thus be treated accordingly.

In the second data mining technique, Association Rules based approaches derive conditional probability measures to determine a degree of support, or confidence, for the validity of a conclusion. That is, probabilities are derived to determine the level of support (designated in terms of a ratio) that given a certain condition, a subsequent condition exits. Furthermore, the probability that the first condition ever occurs is likewise determined. This probability is used to predict how prevalent a condition actually is. For example, if all patients are female then the support of male and complicated is less significant than in the current example. Returning to the data in our sample database, the degree of support of: given that the patient is a male, the type of UTI is complicated, is:

P(Male|Complicated)=(3|3)=1.

Thus, with a probability of 1, if a patient is a male then it is concluded that the type of UTI is complicated. The probability of the patient being male is 3 out of 10 or 30%.

Referencing FIG. 4, a simple decision tree 45 for UTI complication decision-making is illustrated. In the third data mining technique, Classification based approaches, at times referred to as supervised classification, a model for determining the class type of certain conditions is derived from a training set. A common example of this type of a data mining approach is the use of decision trees. Decision trees are flow diagrams, starting at the root, with each path selected based on a given condition. Once a leaf of a tree is reached, a decision is obtained. As shown in FIG. 4, the initial decision criterion is gender. If the patient is male then the UTI is immediately diagnosed as complicated. Otherwise, clearly the patient is female, and her age is the second criterion. If she is under 13 then she is diagnosed as having a complicated UTI. If she is between the ages of 13 and 50 and has had two or fewer UTIs or she is over the age of 50 and this is her first UTI all within a given time period then she is diagnosed as having an uncomplicated UTI. All other cases are complicated. Given this decision tree, the determination of the complexity of a UTI of a new patient can be systematically determined.

In the fourth data mining technique, Clustering approaches, at times referred to as unsupervised classification, the database entries are partitioned into clusters, or sets, of related elements. Using a similarity measure of the attribute values, related entries are grouped and a central value, often called a centroid, is computed. Each derived cluster represents a possible related scenario, e.g., type of antimicrobial used, related demographic information, gender, age, etc. In the present invention, each cluster might likewise have a potential treatment guidance associated with it. Given the database 35 shown in FIG. 3, possible derived clusters include:

Cluster 1:

| | |
|---|---|
| Centroid Representing: | Not complicated: |
| Key Attribute Features: | Female, First UTI, Age between 30 and 46 |
| Members: | {Sara Klein, Jody Stark, Mary Smith, Kelly Jones, Tammy Green} |

Cluster 2:

| | |
|---|---|
| Centroid Representing: | Complicated, Male |
| Key Attribute Features: | Male |
| Members: | {Tom Gross, Fred Schwartz, David Gold} |

Cluster 3:

| | |
|---|---|
| Centroid Representing: | Complicated, Female, Repetitive |
| Key Attribute Features: | Female, Recurrent UTIs |
| Members: | {Sally Weiss} |

Cluster 4:

| | |
|---|---|
| Centroid Representing: | Complicated, Female, Young |
| Key Attribute Features: | Female, Age 11 |
| Members: | {Susan Brown} |

Given a new patient experiencing a UTI, the new patient attributes are evaluated and compared against the key attribute features of the cluster. Those clusters whose key attribute features are similar to the new patient's features are considered related. A diagnosis (as represented above in the first listed centroid for each cluster) corresponding to those clusters is made and the associated potential treatment guidance of the clusters is prescribed.

Obviously, in each of the data mining techniques the identified pathogens and treatments as discussed above will be factored into the comparison and conclusions as a major form of data. Pattern evaluation to determine confidence level in the data and knowledge representation to the health care practitioners can be accomplished via a variety of techniques known in the art.

The system software is designed such that an information collecting staff person or other appropriately trained individual (such as a medical practitioner) can retrieve and sort data by means of a standard search program. Additional levels of complexity can be added to allow the data processing device such as a computer itself to scan the database, analyze data, and generate reports. The reports can be based on predefined statistical parameters established by the medical practitioner affiliated with the service center.

In addition to aiding medical practitioners in predicting which bacterium has caused an infection in a patient and which antimicrobials are useful in treating the infection, the present invention offers many advantages to the health care community. For example, prior to launching new drugs on the market, pharmaceutical manufacturers perform extensive clinical testing and collect data on effectiveness of their drugs and on adverse reactions associated with them. Once the drug is launched, relatively little information is accessible. In the case of infectious diseases such as UTI where antibiotic resistance is a documented problem, pharmaceutical companies could greatly benefit from this type of continuous, broad-based collection of information on their products. A narrowly confined outbreak of resistance may indicate a need for closer observation or suggest that a drug is counter-indicated for a segment of the population. Alternatively, a growing resistance may have serious implications for the future of the product and for strategic planning for new products.

A managed care organization may use the database to establish prescription guidelines or to monitor physician performance. Since the database will contain information relating specific drugs to patient outcomes, the managed care organization may determine that most UTIs in most locations are successfully treated with a low cost antibiotic and that more expensive drugs are unnecessary. The managed care organization could then provide guidelines to participating physicians that the lower cost drug should be prescribed unless certain mitigating factors are present.

Additionally, a computer is programmed to analyze the data and to recommend a course of action to the medical practitioner and/or patient. As an example, a woman has recurrent symptoms of UTI but test results repeatedly indicate no evidence of infection. The woman is advised via report generated by the medical record system data processing device that she must see a urologist for evaluation of other causes for the symptoms. A medical practitioner receives a report informing them that the drugs he/she is prescribing for a certain type of infections are no longer effective and that an alternative should be tried. Moreover, a data processing device, based on the information present in the record system, may generate reports for pharmaceutical companies concerning, for example, the utilization patterns and patient outcomes for a specific drug. These reports could be compiled and the information communicated to a subscribing pharmaceutical company on a pre-determined schedule.

By practice of the techniques according to the present invention, data may be made available to the health practitioners in preanalyzed formats and suggested courses of practice without, or in addition to, the previously taught system of data extraction by direct query from the health practitioner. Knowledge discovery processing, including the above data mining techniques, as set forth herein can be applied to continuously changing data. Data changes may arise from such causes as additional patient data entered in to the system or the discovery of new bacterial resistance. Best practice guidelines for the physician can be derived according to the techniques herein. Potential epidemic threat detection and warning can be accomplished by the present invention through data related to group diagnostic patterns and derived information potentially based on geographic regions, age, weight, profession, etc. Predictive treatment outcome generation via a "virtual patient" can be supported to develop answers to hypothetical scenarios by automatically mining the data to derive potential treatment patterns. Experimentation on a virtual patient or class of groups of patients is supported. Further, given the cleansing process involved in knowledge discovery, error detection, with potential for suggestive correction, is supported.

While the invention has been disclosed with reference to specific embodiments, it is apparent that other embodiments and variations of this invention may be devised by others skilled in the art without departing from the spirit and scope of the invention. Thus, the present invention is intended to be limited only by the appended claims.

We claim:

1. A method for the construction and utilization of a medical records system, comprising:
   collecting epidemiological information of female persons having or previously having a urinary tract infection, wherein the epidemiological information includes identifications of bacterial pathogens, treatment antimicrobials, and antimicrobial efficacy;
   entering and storing the collected epidemiological information in an electronic database, the database including a record of a plurality of different types of bacterial pathogens known for causing urinary tract infections, antimicrobials used for treating the urinary tract infections, and treatment efficacy of the antimicrobials;
   creating an automated knowledge discovery system, including organizing the epidemiological information in the electronic database to make the epidemiological information amenable to data mining;
   receiving through a query function of the database patient epidemiological information from a patient having a urinary tract infection, the patient epidemiological information including at least one symptom of the patient and demographic and personal information for the patient;
   automatically predicting with the knowledge discovery system a bacterial pathogen causing the patient's urinary tract infection from the plurality of different types of bacterial pathogens known for causing urinary tract infections by data mining the organized epidemiological information as a function of similarities of the patient epidemiological information with the organized epidemiological information and without first performing a diagnostic test on a sample from the patient;
   automatically predicting with the knowledge discovery system an antimicrobial treatment for the patient based on the bacterial pathogen prediction of the data mining; and
   automatically issuing to a medical practitioner treating the patient a report including the antimicrobial treatment for the patient based on the bacterial pathogen prediction.

2. The method according to claim 1, further comprising allowing the female persons to self-test for bacterium identification, and entering results of the self-test into the database.

3. The method according to claim 1, further comprising allowing the female persons to self-test for the treatment efficacy, and entering results of the self-test into the database.

4. The method according to claim 1, wherein the data mining comprises a technique selected from Discrimination, Association Rules (Analysis), Classification (Decision Trees), Clustering data mining techniques, and combinations thereof.

5. The method according to claim 1, further comprising:
   providing a kit to each of the female persons for collecting at least one of epidemiological information and a diagnostic sample;
   receiving from the female persons the epidemiological information and a plurality of diagnostic samples;
   evaluating the diagnostic samples to obtain bacterial pathogen information;
   entering and storing the collected epidemiological information and the bacterial pathogen information in the electronic database;
   providing a similar kit to the patient for collecting the patient epidemiological information.

6. The method according to claim 5, further comprising:
   receiving from the female persons a plurality of second diagnostic samples obtained after antimicrobial treatment;
   evaluating the second diagnostic samples to obtain further bacterial pathogen information;
   entering and storing the further bacterial pathogen information in the electronic database.

7. The method according to claim 1, wherein the course of antimicrobial treatment comprises an enumeration of antimicrobials not to be prescribed to the patient.

8. The method according to claim 1, wherein the data mining comprises identifying information common to the female persons who developed an infection from a particular pathogen.

9. The method according to claim 8, wherein the data mining comprises identifying the efficacy of antimicrobials used in treating a particular bacterial pathogen.

10. The method according to claim 1, wherein the data mining comprises identifying the efficacy of antimicrobials used in treating a particular bacterial pathogen.

11. The method according to claim 1, wherein the data mining comprises continuously executing knowledge discovery operations on the data and giving suggestions selected from treatment patterns and epidemiological scenarios, for presentation to a health care practitioner.

12. The method according to claim 11, wherein the suggestions are based at least in part on past health care practitioner decisions entered into the electronic database.

13. The method according to claim 11, wherein the suggestions are based at least in part on past health care practitioner comments regarding a validity or value of given suggestions, the comments being stored as further information in the knowledge discovery system.

14. The method according to claim 1, the knowledge discovery system further providing predictive treatment outcome generation via a virtual patient to develop answers to hypothetical scenarios by automatically mining the data to derive potential treatment patterns for a virtual patient or group of patients.

15. The method according to claim 1, the knowledge discovery system further providing epidemic threat detection through data mining related to group diagnostic patterns and demographic categories.

16. The method according to claim 1, wherein creating the knowledge discovery system comprises data cleaning of the entered epidemiological information for integration of data from several sources.

17. The method according to claim 1, wherein creating the knowledge discovery system comprises data transformation of the entered epidemiological information to a common format.

18. The method according to claim 1, wherein creating the knowledge discovery system comprises data mining of the entered epidemiological information to detect patterns found in the entered epidemiological information.

19. The method according to claim 1, wherein creating the knowledge discovery system comprises pattern evaluation and knowledge representation.

20. The method according to claim 1, wherein creating the knowledge discovery system includes a process comprising iterative refinement of the following steps:
   data cleaning of the entered epidemiological information;
   data transformation of the entered epidemiological information to a common format;
   data mining of the entered epidemiological information; and
   pattern evaluation and knowledge representation of knowledge gained from the data mining.

21. A method for the construction and utilization of a medical records system, comprising:
   collecting epidemiological information of members of a population having or previously having a urinary tract infection, the epidemiological information selected from the group consisting of personal information, demographic information, symptoms, samples, and combinations thereof;
   entering and storing the collected epidemiological information in an electronic database, the database including a record of a plurality of different types of bacterial pathogens known for causing urinary tract infections, antimicrobials used for treating the urinary tract infections, and treatment efficacy of the antimicrobials;
   creating an automated knowledge discovery system including organizing the epidemiological information in the electronic database to provide organized epidemiological information that is amenable to data mining;
   obtaining in a data processing device from a requester epidemiological information of a patient having a urinary tract infection, wherein the requester is a medical practitioner treating the patient and the epidemiological information of the patient includes at least one symptom of the patient and demographic and personal information for the patient and is entered into a query function of the database;
   automatically predicting from the plurality of different types of bacterial pathogens known for causing urinary tract infections a pathogen causing the patient's urinary tract infection using only the data processing device by data mining the organized epidemiological information as a function of similarities of the patient epidemiological information with the organized epidemiological information and without first performing a diagnostic test on a sample from the patient; and
   automatically submitting to the requester the pathogen prediction for prescribing antimicrobial treatment to the patient based on the prediction.

22. The method according to claim 21, wherein the data mining comprises a technique selected from Discrimination, Association Rules (Analysis), Classification (Decision Trees), Clustering data mining techniques, and combinations thereof.

23. The method according to claim 21, wherein collecting prior epidemiological information of members of a population comprises:
   providing a kit to each of a plurality of members of a population having symptoms associated with a urinary tract infection for collecting at least one of prior epidemiological information of and a diagnostic sample from each of the members of the population;
   receiving from the members of a population epidemiological information and a plurality of diagnostic samples;
   evaluating the diagnostic samples to obtain pathogen information.

24. The method according to claim 23, wherein the kit includes a diagnostic test for obtaining the diagnostic sample.

25. The method according to claim 23, wherein the diagnostic samples are forwarded to an evaluating entity.

26. The method according to claim 21, wherein organizing the epidemiological information comprises a data cleaning of the collected epidemiological information.

27. The method according to claim 26, wherein the data cleaning comprises review of the data set, removal or correction of erroneous data, and the transformation of the data to a common format to support the processing of the data.

28. A method for the construction and utilization of a medical records system, comprising:
   distributing a plurality of first kits to a population presenting symptoms of a urinary tract infection, wherein the first kits are for establishing and recording epidemiological data for the population;

establishing and recording epidemiological data of the population, the epidemiological data including the symptoms in the population, demographic and personal information in the population, incidence of bacterial pathogens causing symptoms in the population, use of a medicine for treatment of the bacterial pathogens in the population, and results of treatment via the medicine in the population;

building in a searchable database an epidemiological profile of the population via data mining of the epidemiological data, the database including a record of a plurality of different types of bacterial pathogens known for causing urinary tract infections, antimicrobials used for treating the urinary tract infections, and treatment efficacy of the antimicrobials;

distributing a second kit to an undiagnosed patient presenting symptoms of a urinary tract infection for establishing and recording epidemiological data for the undiagnosed patient;

receiving the epidemiological data for the undiagnosed patient in a data processing device in combination with the database, the epidemiological data including at least one symptom for the undiagnosed patient and demographic and personal information for the undiagnosed patient; and the data processing device automatically predicting from the plurality of different types of bacterial pathogens known for causing urinary tract infections a bacterial pathogen causing the undiagnosed patient's urinary tract infection from identification of the bacterial pathogens recorded in the searchable database by comparing the epidemiological data for the undiagnosed patient to the epidemiological profile of the population and without first performing a diagnostic test on a sample from the patient; and automatically issuing to a medical practitioner treating the patient a report including the antimicrobial treatment for the patient based on the bacterial pathogen prediction.

29. The method according to claim 28, wherein the data mining comprises a technique selected from Discrimination, Association Rules (Analysis), Classification (Decision Trees), Clustering data mining techniques, and combinations thereof.

30. The method according to claim 28, further comprising automatically prescribing with the knowledge discovery system a course of treatment for the patient based on the pathogen prediction of the data mining.

31. The method according to claim 30, wherein the course of treatment comprises an enumeration of antimicrobials not to be prescribed to the patient.

* * * * *